(12) United States Patent
Whitman et al.

(10) Patent No.: US 8,012,170 B2
(45) Date of Patent: Sep. 6, 2011

(54) DEVICE AND METHOD FOR CONTROLLING COMPRESSION OF TISSUE

(75) Inventors: Michael P. Whitman, New Hope, PA (US); Donald Malinouskas, Monroe, CT (US); David A. Zeichner, Oxford, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 207 days.

(21) Appl. No.: 12/430,780

(22) Filed: Apr. 27, 2009

(65) Prior Publication Data

US 2010/0270355 A1    Oct. 28, 2010

(51) Int. Cl.
*A61B 17/068* (2006.01)
(52) U.S. Cl. ....... 606/219; 606/153; 227/19; 227/175.1; 227/176.1
(58) Field of Classification Search .............. 227/19, 227/175.1, 176.1, 175.2, 180.1; 606/151, 606/153, 219
See application file for complete search history.

(56) References Cited

U.S. PATENT DOCUMENTS

| | | | |
|---|---|---|---|
| 5,383,880 A | | 1/1995 | Hooven |
| 5,535,937 A * | | 7/1996 | Boiarski et al. ............ 227/175.3 |
| 5,810,811 A * | | 9/1998 | Yates et al. .................. 606/50 |
| 6,533,157 B1 * | | 3/2003 | Whitman ................. 227/175.1 |
| 6,698,643 B2 * | | 3/2004 | Whitman ................. 227/180.1 |
| 6,793,652 B1 * | | 9/2004 | Whitman et al. ............... 606/1 |
| 6,981,941 B2 * | | 1/2006 | Whitman et al. ............... 600/1 |
| 7,023,159 B2 * | | 4/2006 | Gorti et al. ................. 318/432 |
| 7,246,734 B2 * | | 7/2007 | Shelton, IV ............. 227/175.1 |
| 7,416,101 B2 * | | 8/2008 | Shelton et al. .......... 227/175.1 |
| 7,464,847 B2 * | | 12/2008 | Viola et al. ............. 227/175.2 |
| 7,568,603 B2 * | | 8/2009 | Shelton et al. .......... 227/178.1 |
| 7,717,312 B2 * | | 5/2010 | Beetel ................... 227/175.1 |

FOREIGN PATENT DOCUMENTS

| EP | 1980215 | 10/2008 |
|---|---|---|
| EP | 2027819 | 2/2009 |

OTHER PUBLICATIONS

European Search Report for EP 10 25 0941 date of completion is Aug. 20, 2010 (3 pages).

* cited by examiner

*Primary Examiner* — Scott A. Smith (57) ABSTRACT

A method and device for controlling the compression of tissue include clamping tissue between a first clamping member and a second clamping member by driving at least one of the clamping members with an electric motor toward a predetermined tissue gap between the clamping members and, during the clamping, monitoring a parameter of the electric motor indicative of a clamping force exerted to the tissue by the clamping members. The method and device include, during the clamping, controlling the electric motor, based on the monitored parameter, to limit the clamping force to a predetermined maximum limit.

22 Claims, 8 Drawing Sheets

DEVICE AND METHOD FOR CONTROLLING COMPRESSION OF TISSUE

FIELD OF THE INVENTION

The present invention relates generally to medical devices. More specifically, the present invention relates to a device and method for controlled tissue compression.

BACKGROUND INFORMATION

Some surgical procedures require the compression, e.g., clamping, of a patient's tissue. Such procedures may include, e.g., anastomosing, stapling, and resecting of tissue. For example, where cancerous tissue is identified in a patient's gastrointestinal tract, the cancerous tissue may need to be surgically removed. Where, for example, the cancerous tissue is located on the colon and is accessible by surgical instrumentation, the surgeon may make an incision in the patient's abdomen to allow access to the bowel. The surgeon may then use a linear cutting and stapling device, such as that described in U.S. patent application Ser. No. 12/235,362, which is expressly incorporated herein in its entirety by reference thereto, to cut and staple the colon tissue on opposite sides of the cancerous portion to be removed. In this procedure, the colon is externally clamped (e.g., between opposed jaws) to compress the tissue. While the tissue is compressed, a cutter and a stapler are activated to make a linear cut and apply typically two linear rows of staples in the areas adjacent the cut. The stapling thus closes both open ends of the portion of the bowel to be removed, as well as providing a temporary closure of the two cut ends of the bowel. This closure limits exposure of the surrounding tissue to the interior of the bowel, thus limiting the risk of infection. After the cutting and stapling procedure, the cancerous portion of tissue may be removed from the patient's body.

After the resection of the cancerous tissue, the surgeon may employ an anastomosing and stapling device, e.g., a circular stapler/cutter, such as that described in U.S. patent application Ser. No. 10/785,682, which is expressly incorporated herein in its entirety by reference thereto. During this procedure a head portion is positioned within the colon adjacent one of the cut ends and a base or shaft portion is positioned within the colon adjacent the other cut end. The head portion and the base portion may be coupled via a shaft and/or cable that extends out of one cut end and into the other. Via this coupling, the surgeon is able to actuate the anastomosing and stapling device to draw the head portion and the base portion together. After the two cut ends of the colon contact each other, the actuation continues such that the two portions of the colon are clamped together at an annular area of contact. While clamped, the anastomosing and stapling device may be further actuated to apply an annular ring of staples into the compressed tissue. The device may also cut excess tissue disposed within the colon. The head portion and the base portion are then moved apart and the anastomosing and stapling device removed from the patient.

To achieve effective stapling in the above procedures, the tissue must be compressed to the extent that there is an adequately small tissue gap, e.g., one millimeter, between the faces of the tool. If the clamping structures of the instrument are exposed to enough force, maintaining a uniform target tissue gap across the length of tissue to be stapled may be difficult or even impossible. For example, where the clamping structures are cantilevered jaws of a linear stapler, the jaws may splay outwardly from each other under high clamping forces. Where one or both of the jaws splay in this manner, the tissue gap typically increases toward the distal ends of the jaws. Where this tissue gap exceeds an acceptable range, staples may not adequately close the tissue to prevent contamination. This may be result from, e.g., the initial stapled gap being too large and/or failure of the staple (e.g., separation from one or more of the portions of stapled tissue) due to improper formation resulting from, e.g., too large a gap between a staple pusher and an anvil that closes the staple.

Such problems with the stapling procedure may lead to contamination of tissue (e.g., contamination of tissue adjacent the bowel with bowel contents), which may contribute to infection and/or sepsis. Such problems with the stapling procedure may also lead to, e.g., failure of the anastomosis (e.g., where the stapled tissues separate) and/or excessive bleeding due to improper tissue closure. Moreover, these problems may require additional, repeated, and/or prolonged surgery along with any increased risks associated therewith. As reported by the United States Food and Drug Administration (see "Surgical Stapler Information," "Other Data," at http://www.fda.gov/cdrh/surgicalstapler/other_data.html, last updated Jul. 21, 2004), infection, sepsis, anastomosis failure, and bleeding are substantial problems that arise in stapling procedures and may potentially lead to serious injuries, or even death, to some patients. It is thus desirable to minimize these problems.

Moreover, when performing the compression, a constant closing rate (e.g., the closing rate between jaws of a linear stapler or between the head and base portion of a circular stapler/cutter) may exert a high level of power into the clamped tissue. This high level of power may result in excess tissue trauma. It is thus desirable to limit this trauma, e.g., by effectively controlling the power applied to the tissue. Further, it is desirable to determine whether the tissue to be clamped is compressible.

U.S. Patent Application Publication No. 2009/0057369 describes a device that uses continuous measurements from a linear force switch housed in an anvil neck. The switch is calibrated to activate when a given load is applied. The given load is set to correspond to a desired pressure that is to be applied to the particular tissue before stapling can occur. Interfacing this switch with a processor provides firing of staples only within a compression range. Such devices and control methods do not allow for a continuous closure or monitoring of power going into the compressed tissue.

Further, it is desirable to monitor and track structural fatigue in clamping members in a simple and reliable manner.

It is additionally desirable to identify proper staple filing in a simple and reliable manner.

SUMMARY

Example embodiments of the present invention provide a device and method for controlling compression of tissue.

According to an example embodiment of the present invention, a method includes clamping tissue between a first clamping member and a second clamping member by driving at least one of the clamping members with an electric motor toward a predetermined tissue gap between the clamping members. The method also includes, during the clamping, monitoring a parameter of the electric motor indicative of a clamping force exerted to the tissue by the clamping members. The method also includes, during the clamping, controlling the electric motor, based on the monitored parameter, to limit the clamping force to a predetermined maximum limit.

The predetermined maximum limit may be selected based on predetermined properties of the tissue to be clamped.

The predetermined maximum limit may be selected to limit trauma to the clamped tissue to a predetermined acceptable level.

The predetermined maximum limit may be below a predetermined deflection limit of the at least one of the clamping members.

The controlling may include adjusting a voltage applied to the electric motor. The controlling may include limiting the current driving the electric motor, e.g., to a predetermined maximum value.

The monitoring may include measuring a current driving the electric motor.

The method may include, prior to the clamping, measuring current due to frictional losses associated with moving the clamping members and subtracting the frictional losses from the current measured during the clamping.

The method may include, prior to the clamping, measuring a current offset.

The method may include subtracting the current offset from the current measured during the clamping.

The predetermined maximum limit may be selected to prevent the force from reaching a yield force.

The predetermined maximum limit may be selected to prevent the clamping members from splaying.

The method may include using a profile of the monitored parameter to monitor and track structural fatigue in at least one of the clamping members. The profile may be compared to a normal parameter signature.

The surgical instrument may be a surgical stapler and one of the clamping members may be an anvil arranged to form surgical staples.

The method may include using a profile of the monitored parameter to identify whether all of the staples of a staple cartridge have fired.

The method may include using a profile of the monitored parameter to identify at least one of staple misfires, an absence of staples in a staple cartridge, and staple jams.

The controlling may include, e.g., determining a motor velocity, determining a motor position, and determining a net motor current attributable to the compression by subtracting out a current offset and current due to frictional losses. The controlling may also include determining a velocity drive based on the determined velocity, determining a position drive based on the determined position, and determining a current drive based on the determined net motor current. The controlling may also include applying the smallest of the velocity drive, the position drive, and the current drive to the motor.

The method may include detecting the presence of an incompressible object based on the motor velocity.

The controlling may include adjusting a driving speed of the motor to limit the clamping force to the predetermined maximum limit.

According to an example embodiment of the present invention, a surgical device includes a first clamping member, a second clamping member, and an electric motor configured to drive at least one of the first and second clamping members toward a predetermined tissue gap between the clamping members. The device also includes a control system to monitor a parameter of the electric motor indicative of a clamping force exerted to the tissue by the clamping members and to control the electric motor, based on the monitored parameter, to limit the clamping force to a predetermined maximum limit.

The predetermined maximum limit may be selected based on predetermined properties of the tissue to be clamped.

The predetermined maximum limit may be selected to limit trauma to the clamped tissue to a predetermined acceptable level.

The predetermined maximum limit may be below a predetermined deflection limit of the at least one of the clamping members.

The surgical device may be arranged as at least one of (a) a linear surgical stapler, (b) a circular surgical stapler, and (c) a right-angle linear cutter. It should be appreciated that the surgical device may be arranged as an surgical device including clamping components, including staplers, ligators, etc.

The surgical device may include a current sensor to determine a current driving the electric motor, a velocity sensor to determine the rotational velocity of the electric motor, and a position sensor to determine at least one of the position of an output of the motor and a relative position of the first and second clamping members.

The control unit may be adapted to control the electric motor by adjustment of a driving speed of the motor to limit the clamping force to the predetermined maximum limit.

According to an example embodiment of the present invention, a surgical device is configured to monitor a parameter of an electric motor indicative of a clamping force exerted on tissue being clamped, control the electric motor to determine if a predetermined maximum limit is reached for the clamping force and limit the parameter of the electric motor, and monitor the clamping force to determine variations in the clamping force and allow for the electric motor to reactivate once the clamping force exerted on the tissue has fallen below the predetermined maximum limit.

According to an example embodiment of the present invention, a surgical device is configured to control a compressive force of a first clamping member and a second clamping member toward a predetermined tissue gap and, once said tissue gap is attained, deploy at least one of tissue fasteners, energy, and adhesive fluids so that said tissue will remain approximated during a healing process.

According to an example embodiment of the present invention, a surgical device includes a clamping mechanism configured to clamp tissue, an electric motor configured to drive the clamping mechanism, and a control system. The control system is configured to: monitor a parameter of the electric motor indicative of a clamping force exerted on tissue being clamped; control the electric motor to determine if a predetermined maximum limit is reached for the clamping force and limit the parameter of the electric motor, and monitor the clamping force to determine variations in the clamping force and allow for the electric motor to reactivate once the clamping force has fallen below the predetermined maximum limit.

According to an example embodiment of the present invention, a surgical device includes a first clamping member, a second clamping member, and a control system. The control system is configured to: control a compressive force of the first and second clamping members toward a predetermined tissue gap between the first and second clamping members; and, once the tissue gap is attained, deploy at least one of tissue fasteners, energy, and adhesive fluids so that the tissue will remain approximated during a healing process.

An example method for controlling compression of tissue in accordance with the present invention includes positioning tissue in a tissue compression mechanism, e.g., the jaws of a linear cutting and stapling device or the anvil and base of a circular cutting and stapling device. The method also includes compressing the tissue according to a closing rate.

The method further includes determining the instantaneous energy, or power, and/or accumulated energy, or power, applied to the tissue during compression. The method further includes reducing the closing rate when the imparted power increases, e.g., to a predetermined level. The measuring may include measuring the current applied to a direct current motor. The current may be measured continually, e.g., at a fixed interval, over the course of the compression. The closure rate may be adjusted so that the power imparted into the tissue remains constant over a portion of the compression.

An example device for controlling compression of tissue in accordance with the present invention may include a clamping or compression mechanism. The compression mechanism may be any appropriate mechanism, e.g., rotating or parallel jaws, an anvil and base of a circular stapling and cutting mechanism, and the like. The compression mechanism is actuated by an actuator which may include one or more electric motors which may be disposed in a remote console and/or the housing of the device. Power may be transferred from the actuator to the compression mechanism by any appropriate structure, e.g., one or more rotating shafts arranged to transmit rotational force. Where the actuator includes a direct current motor, the control system, e.g., a digital and/or analog control system, may control the current going into the actuator by altering the voltage applied thereto. The control system may be structured and/or programmed to limit the current going into the motor. The control system may be programmed to calculate the power applied to the tissue based on the measured current going into the motor as indicated by a current sensor. The control system may be programmed to calculate the rate of closure of the compression mechanism based on the voltage input.

Moreover, the controller may be programmed to reduce the rate of closure by altering, e.g., lowering, the voltage input into the actuator, in order to limit the power going into the tissue and/or maintain the power going into the tissue at a constant level.

Further details and aspects of example embodiments of the present invention are described in more detail below with reference to the appended figures.

DETAILED DESCRIPTION

During compression of a patient's tissue, hydraulic effects are present as a result of the composition (e.g., the presence of fluids, etc.) of the tissue. In this regard, hydraulic resistance may be measured and used as feedback for the closing of the clamping elements.

Figure 6A:
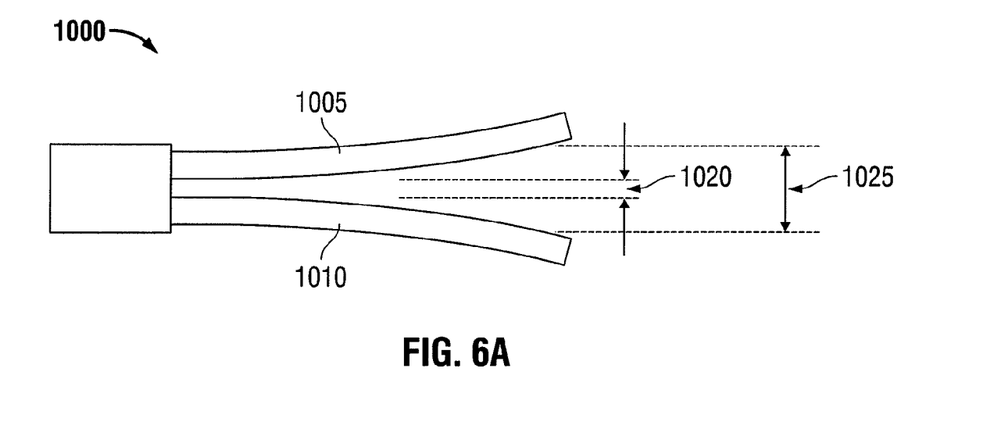
FIGS. 6a and 6b schematically illustrate a splaying effect of jaws of a stapling device.
Figure 6B:
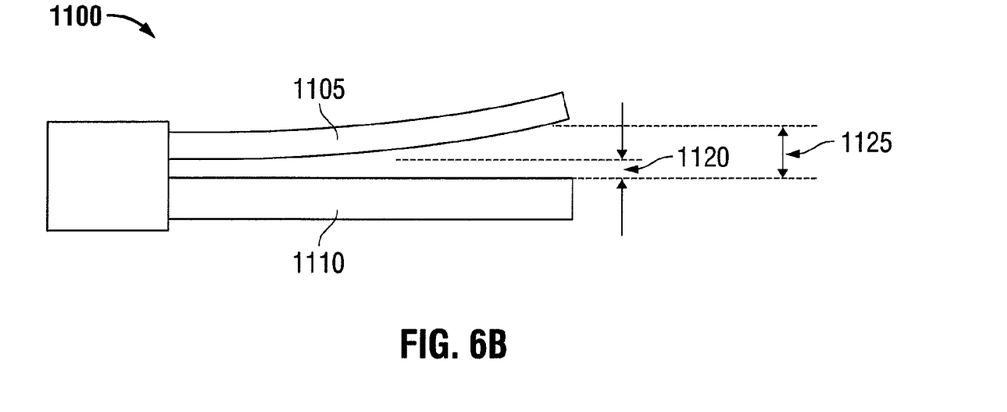

When clamping the patient's tissue, forces exerted through the clamping device, e.g., a linear stapler, and the tissue may reach an unacceptably high level. For example, when a constant closure rate is employed, the force may become high enough to cause excess trauma to the clamped tissue and may cause deformation in the clamping device such that an acceptable tissue gap is not maintained across the stapling path. For example, an acceptable tissue gap may be in the range of, e.g., 1 mm±0.4 mm, $$1 \text{ mm} \frac{+0.4}{-0.3} \text{ mm}$$

(0.7 mm to 1.4 mm), etc. Referring to FIGS. 6a and 6b, linear surgical staplers 1000 and 1100 are schematically illustrated when exerting a clamping force on a section of tissue.

As illustrated, the high level of force exerted by the jaws of the staplers 1000 and 1100 results in a splaying effect, which has been exaggerated in FIGS. 6a and 6b for illustration purposes. Referring to FIG. 6a, a pair of opposed jaws 1005 and 1010 form a target tissue gap 1020 only at a proximal portion, whereas the distal ends of the jaws 1005 and 1010 are splayed outwardly away from each other, resulting in an expanded tissue gap 1025 at a distal portion. This splaying causes the jaws 1005 and 1010 to deviate from a parallel alignment, which may lead to an unacceptably large tissue gap where staples are applied toward the distal ends of the jaws 1005 and 1010, which in turn may result in the aforementioned difficulties, such as, e.g., leakage, contamination, and failed staple connections. This splaying results from exceeding a yield force that causes the jaws to deviate from the parallel alignment relative to each other.

FIG. 6b shows a comparable effect, but where the splaying occurs primarily in a first jaw 1105 that is structurally weaker than a second jaw 1110. This again leads to an unacceptably large tissue gap 1125 that substantially exceeds a target tissue gap 1120.

Figure 1:
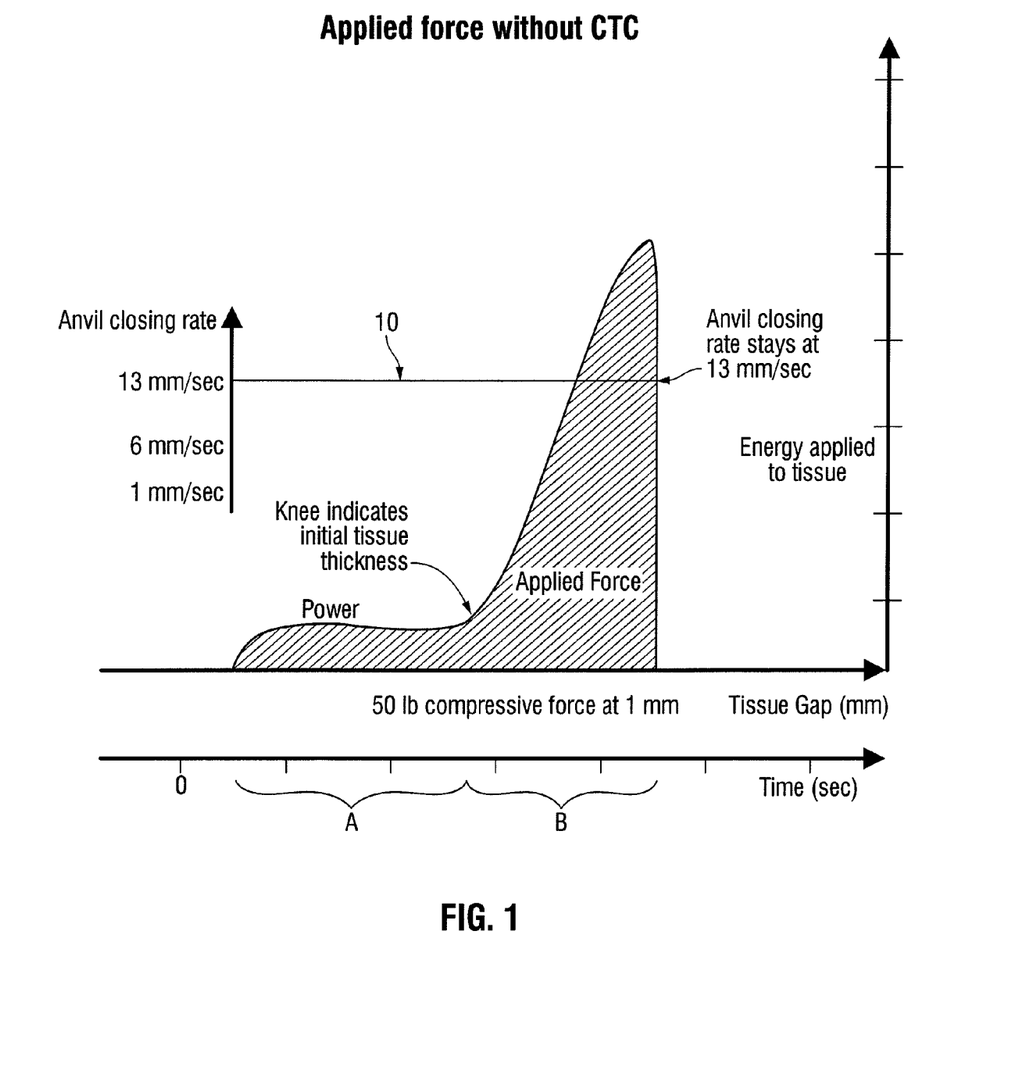
FIG. 1 is a graph illustrating the power applied to tissue during compression at a constant anvil closing rate.

FIG. 1 is a graph illustrating the power applied to tissue during compression at a constant anvil closing rate. The compression begins at an initial open state, wherein the clamping members or elements move a distance prior to compression of the tissue therebetween. Region A represents the time during which the clamping elements move from the initial open state to the beginning of tissue compression and region B represents the time period during which the tissue is compressed from an initial thickness to a target thickness, in this case 1 mm tissue thickness (corresponding to a 1 mm tissue gap between the clamping elements). Regions A' and B' are delineated by a "knee" that indicates the beginning of the compression with the tissue at its initial thickness. The power, and in turn the force, imparted into the tissue rises sharply with respect to time until reaching a peak value. Line 10 indicates the closing rate of the clamping members (indicated in FIG. 1 as Anvil Closing Rate), which is constant between the initial open state and the target tissue gap of 1 mm. The hatched area under the power curve indicates the total energy exerted during the clamping procedure.

Figure 2:
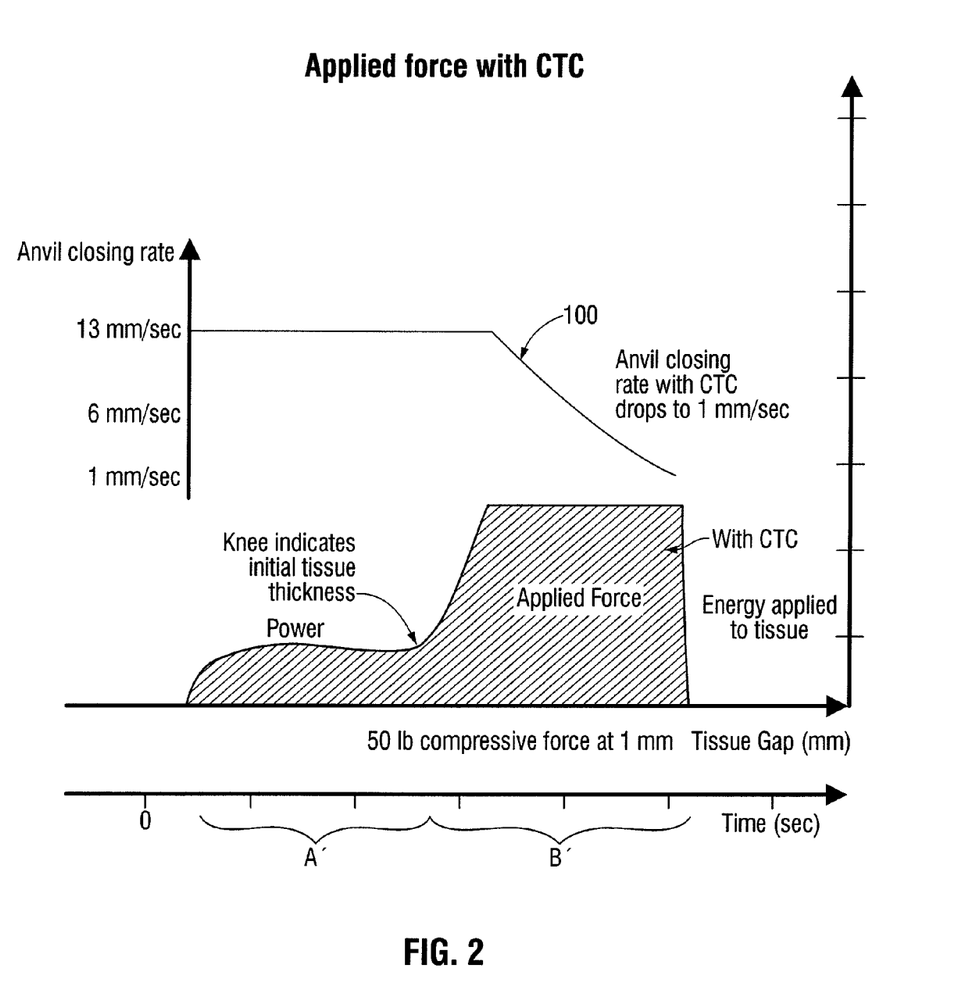
FIG. 2 is a graph illustrating the power applied to tissue during compression according to an example embodiment of the present invention.

FIG. 2 is a graph illustrating the power applied to tissue during compression according to an example embodiment of the present invention. As with the device and method corresponding to the graph of FIG. 1, the compression as illustrated in FIG. 2 begins at an initial open state, in which the clamping members or elements move a distance prior to compression of the tissue therebetween. Region A' represents the time during which the clamping elements move from the initial open state to the beginning of tissue compression, and region B' represents the time period during which the tissue is compressed from an initial thickness to a target thickness, in this case 1 mm tissue thickness (corresponding to a 1 mm tissue gap between the clamping elements). A' and B' are delineated by a "knee" that indicates the beginning of the compression with the tissue at its initial thickness. During the period designated A', the clamping elements close at a constant rate of, e.g., 13 mm/sec. It should be appreciated, however, that any appropriate rate may be employed and need not be constant over the entire period A'. The hatched area under the power curve indicates the total energy exerted during the clamping procedure.

In contrast to FIG. 1, FIG. 2 illustrates that it is determined that the power applied to the tissue is increasing and, at a certain level, the closing rate is decreased, in this example, from 13 mm/sec to 1 mm/sec, effectively increasing the time required to compress the tissue and decreasing the power applied to the tissue. The closing rate is illustrated in FIG. 2 as line 100. In this example, the power applied to the tissue is held constant, although it should be appreciated that according to certain example embodiments, the power may fluctuate.

Figure 3:
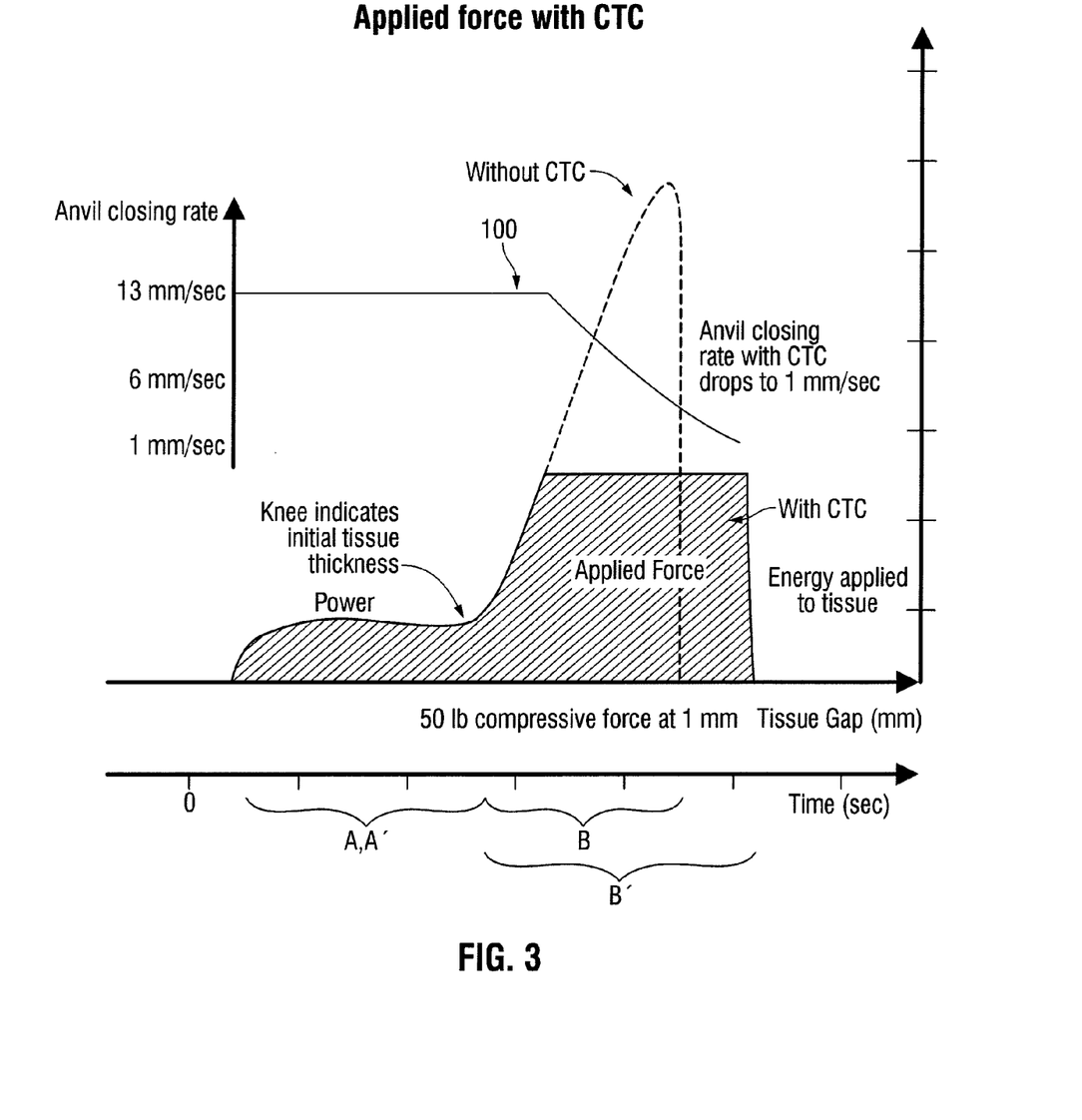
FIG. 3 is a superposition of the graphs of FIG. 1 and FIG. 2.

FIG. 3 is a superposition of the graphs of FIG. 1 and FIG. 2. In contrast to the system and method reflected in FIG. 1, the peak power imparted into the tissue according to FIG. 2 is much lower. Based on the imparted power, the force exerted by the surgical device (or a parameter related to or proportional to the force) may be calculated. In this regard, the power may be limited such that the force exerted through the surgical device, e.g., through the jaws of a linear stapler, do not exceed a yield force or pressure that results in splaying of the jaws such that the tissue gap is not within an acceptable range along the entire stapling length when in the fully closed position. For example, the jaws should be parallel or close enough to parallel that the tissue gap remains within the acceptable or target range for all staple positions along the entire length of the jaws. Further, the limitation of the exerted power avoids, or at least minimizes, trauma or damage to tissue.

In this example, the total energy exerted in the method of FIG. 1 is the same as the total energy exerted in the method of FIG. 2, i.e., the areas under the power curves of FIGS. 1 and 2 are the same or substantially the same. The difference in the power profiles utilized is, however, substantial, as the peak power is much lower in the example of FIG. 2 as compared to FIG. 1.

The limiting of power is achieved in the example of FIG. 2 by slowing the closing rate, as illustrated by line 100. It is noted that the compression time B' is longer than the closing time B. As illustrated in FIGS. 1 to 3, a device and method that provides a constant closure rate achieves the same 50 lb of compressive force at the same 1 mm tissue gap as the device and method reflected in connection with FIG. 2. While the device and method that provide for a constant closure rate (FIG. 1) may achieve the compressive force at the desired tissue gap in a shorter time period as compared with FIG. 2, as illustrated, e.g., in FIG. 1, this results in the spike in power applied to the tissue. In contrast, the example embodiment illustrated, e.g., in connection with FIG. 2, begins slowing the rate of closure to limit the amount of power applied to the tissue below a certain level. By limiting the power applied to the tissue, tissue trauma may be minimized with respect to the system and method reflected in FIG. 1.

According to example embodiments, the device and method may be implemented by determining the power or force applied to the tissue by measurement of the current applied to an actuator, since the current is proportional to the torque output of the motor. In this regard, losses based on the instrument, e.g., due to friction between moving parts, etc., may be subtracted from the power applied to the driving motor to more accurately determine the power that is being imparted into the tissue. These losses to be backed out may be determined in any appropriate manner such as, e.g., testing the instrument or components of the instrument, using known qualities of the instrument or components of the instrument, and/or performing calculations based on the testing and/or known qualities. For example, the instrument may be driven in an unloaded condition to obtain a baseline measurement of power or current required to drive the instrument and its associated components. Thereafter, power or current in excess of the baseline corresponds to the power that is applied to the tissue during compression.

Where, for example, the actuator is a direct-current electric motor, the power applied to the motor may be determined based on a measurement of the current required to drive the motor. The losses due to the instrument are then backed out to determine the power imparted into the tissue during the compression. This measurement allows a source of feedback when compressing the tissue. The power applied to the motor may be continually monitored with calculations being performed on a continuous basis. This allows, for example, the power or force applied to the tissue to be accurately controlled, e.g., by adjusting the voltage going into the motor. In this example feedback control system, the consumed current would be the feedback, with the voltage being adjusted to achieve a desired current. The example illustrated in the graph of FIG. 2 uses this control system to reduce the rate of closure when the determined power hits a particular level, e.g., a predetermined power level selected to prevent unacceptable levels of tissue trauma.

Figure 4:
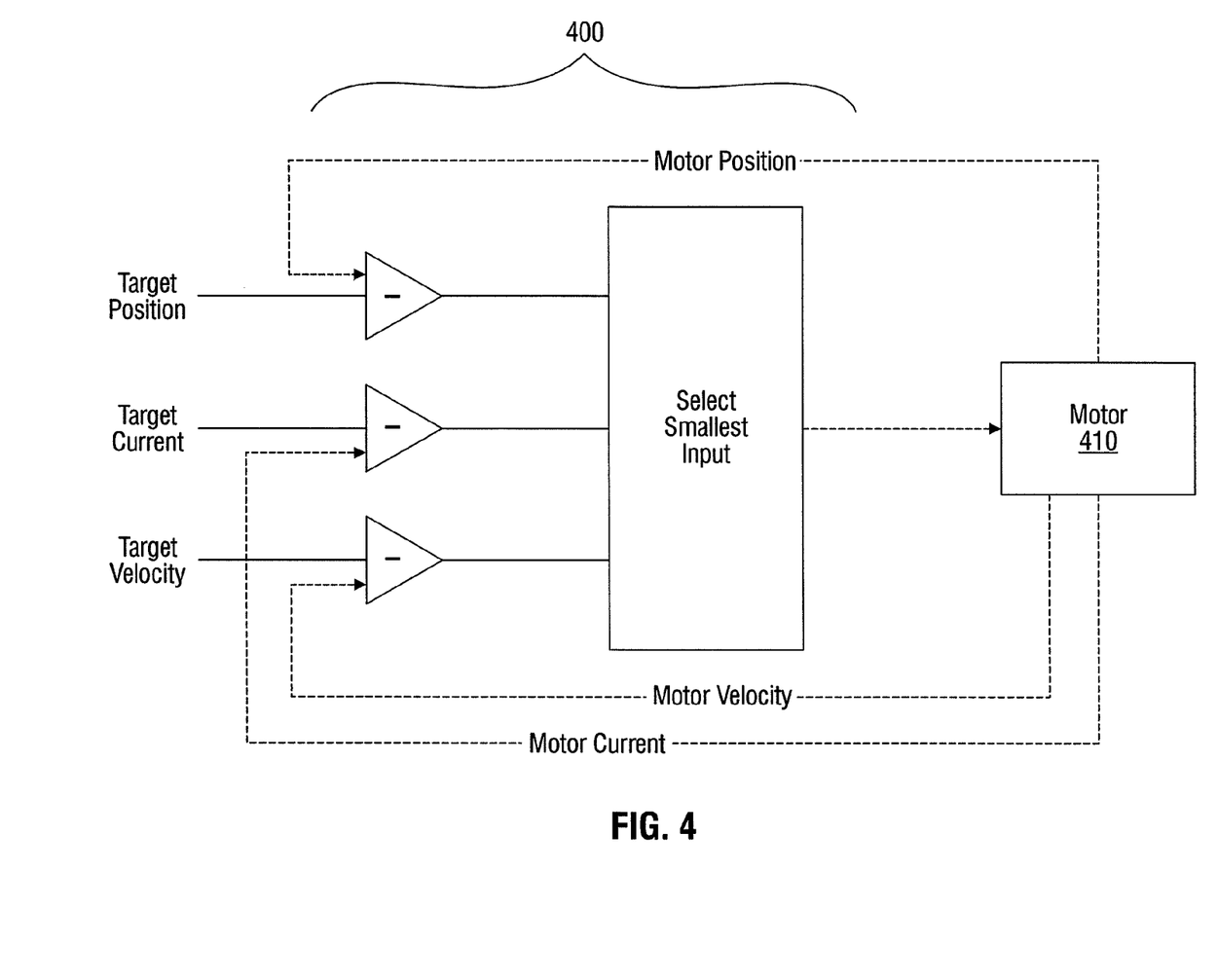
FIG. 4 is a schematic illustration of a control system according to an example embodiment of the present invention.

FIG. 4 is a schematic illustration of a control system according to an example embodiment of the present invention. A controller 400 controls a motor 410 that drives a clamping operation, e.g., clamping of the jaws of a linear surgical stapler. A target position, a target current, and a target velocity are input into the controller 400, e.g., by a particular control program and/or manual input by a surgeon or operator. The controller 400 receives motor position, motor velocity, and motor current signals as feedback for controlling the motor 410. As discussed in greater detail below, the controller 400 according to this example selects the smallest input for controlling the motor 410.

Figure 5:
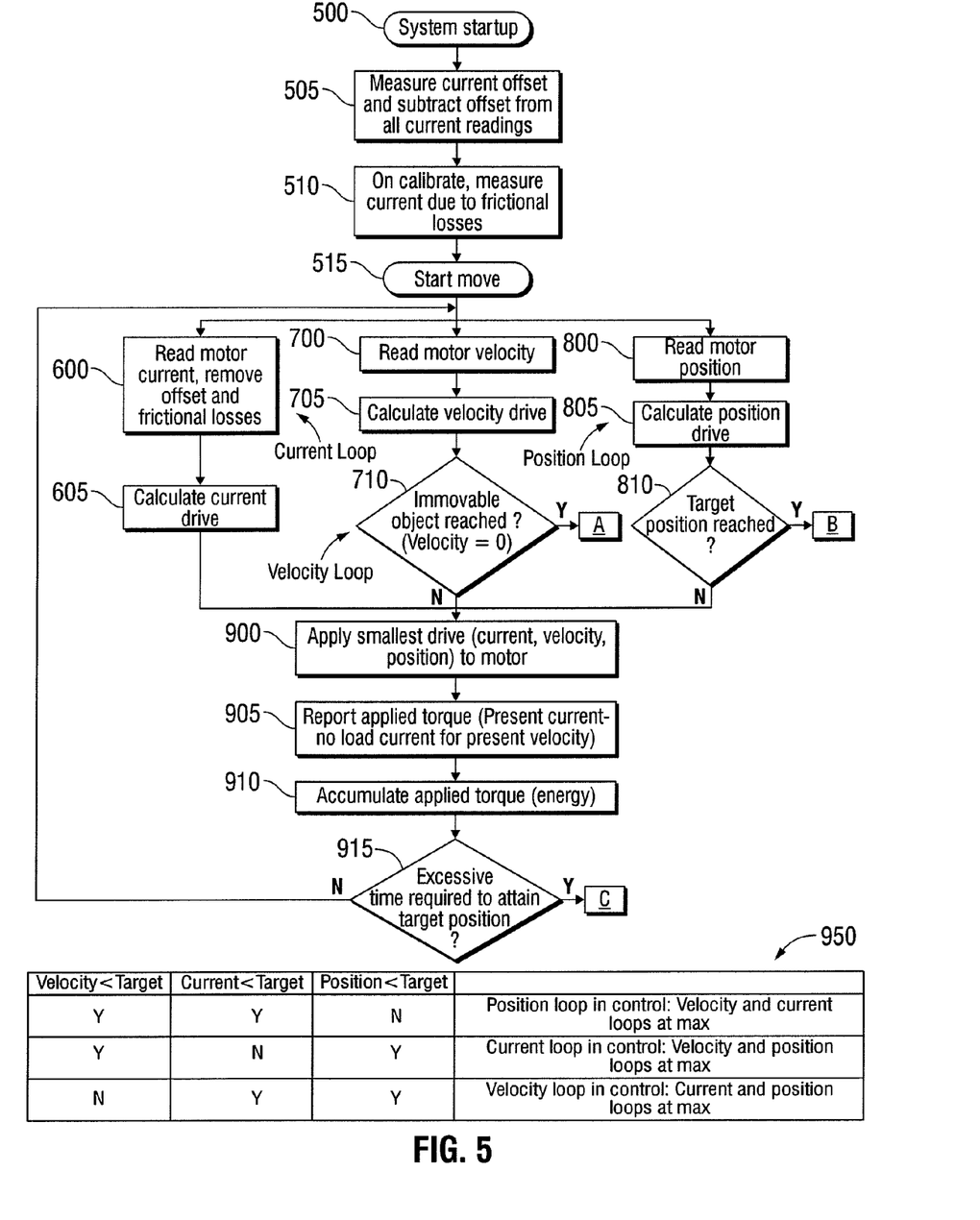
FIG. 5 is a flowchart illustrating a method according to an example embodiment of the present invention.

FIG. 5 is a flowchart illustrating a method according to an example embodiment of the present invention. System startup occurs at 500. After system startup, current offset is measured and set to be subtracted from all current readings so that all readings are taken from a zero or near-zero baseline. At 510, calibration occurs, including measuring current due to frictional losses, e.g., friction in the motor and the drive components that convert the rotational force of the motor into the clamping force exerted through the instrument, e.g., the force exerted through the jaws of a linear stapler. The calibration may be performed by measuring the current corresponding to different motor speeds under a no-load condition, i.e., during unobstructed movement. It should be appreciated that the offset measurement and calibration may be performed every time the system starts up and/or the values obtained may be stored to be used in subsequent procedures using the same equipment. For example, the control system may require remeasuring of these values after a given time period, number of uses, and/or number of system startups.

After calibration, the clamping procedure may begin. When the tissue to be clamped is disposed in the clamping portion of the surgical instrument, movement is started at 515. The exemplary method then performs a current loop, a velocity loop, and a position loop. These loops need not be performed in any particular order and two or all three of the loops may be performed simultaneously, or substantially simultaneously, in some examples.

For the current loop at 600, motor current is read, e.g., according to the signal of a current sensor arranged to sense the current driving the motor. The offset and frictional losses, determined at 505 and 510, are removed or subtracted out. In this manner, the portion of the current that is applied in response to the tissue clamping is determined. At 605, a current drive is calculated using a current drive formula. For example, the current drive may be determined by $K_1$*(target current—motor current), where $K_1$ is selected based on desired control performance for controlling the motor current.

For the velocity loop at 700, the motor velocity is determined. The velocity is determined either by reading a signal from a velocity signal or any other appropriate manner, e.g., from position and time data. At 705, a velocity drive is calculated using a velocity drive formula. For example, the velocity drive may be determined by $K_2$*(target velocity−motor velocity), where $K_2$ is selected based on desired control performance for controlling the motor velocity. At 710, it is determined whether an immovable object has been reached. In this regard, a velocity value of zero is indicative of an immovable object or obstruction being reached by the clamping device. If an obstruction has been reached, the driving of the motor is then stopped at A. Otherwise, the control continues. It should be appreciated that this determination may be made before, after, and/or at the same time as the calculation of the velocity drive.

For the position loop at 800, the motor position is read. The motor position may be determined, e.g., by an encoder or a resolver coupled to an output of the motor, or any other appropriate manner. At 805, a position drive is calculated using a position drive formula. For example, the position drive may be determined by $K_3$*(target position−motor position), where $K_3$ is selected based on desired control performance for controlling the motor position.

At 810, it is determined whether a target position has been reached. If the target position has been reached, the control loop exits at B. At B, the output to the motor may be stopped (e.g., where the tissue is clamped using drivers that are not back-drivable by residual pressures exerted by the clamped tissue or by the force of a staple being driven and formed between the clamping members) and/or the motor may be controlled to output an amount of force needed to maintain the motor at the target position, which generally corresponds to the target tissue gap in the examples described above. If the target position has not been reached, the control continues. It should be appreciated that the determination of whether the target position has been reached may be made before, after, and/or at the same time as the calculation of the position drive. Further, it should be appreciated that the relative position of the clamping elements, e.g., jaws, or any intermediate component, e.g., a driver, may be used as a positional input.

After the three control loops, the calculated current drive, velocity drive, and position drive, are compared, and the smallest drive is applied to the motor at 900. At 905, the applied torque, which is proportional to and determined from the motor current after subtracting out the offset and frictional losses, is reported. At 910, the applied torque is accumulated to calculate the energy applied to the tissue.

Chart 950 illustrates control prioritization for three different situations. In the first situation, the motor velocity and motor position are below their respective targets, while the motor position is not. In this situation, the position loop controls, while the velocity and current loops are set to maximum values. In the second situation, the velocity and position loops are below their respective targets, while the current loop is not. In this situation, the current loop controls the output, while the velocity and position loops are set to maximum values. In the third situation, the current and position loops are below their respective targets, while the velocity is not. In this situation, the velocity loop controls, while the current and position loops are at maximum values.

It is determined at 915 whether an excessive time is required to attain the target position. This determination may be made by, e.g., examining the amount of time that has elapsed up until the decision 915, a predicted total amount of time based on the elapsed time and the control profile (e.g., current, velocity, and position), and/or any other appropriate manner. If it is determined that the required time is excessive, the exemplary control method exits at C. At C, the control output to the motor may stop or another control method may be employed, e.g., to reverse the position of the motor. For example, the motor may be driven to move the jaws of a linear stapler to an open position so that the surgeon or operator may remove the surgical device or move the jaws to a different portion of tissue that may be easier to clamp. In other words, at C a request or requirement user intervention may be triggered.

If it is determined that an excessive time is not required, the control system again executes the current, velocity, and position loops at 600, 700, and 800, respectively. This loop continues until one of the events A, B, and/or C occurs to break the loop. It should be appreciated, however, that additional conditions may be implemented to break the loop, e.g., a manual override, a sensor error, etc.

Figure 7A:
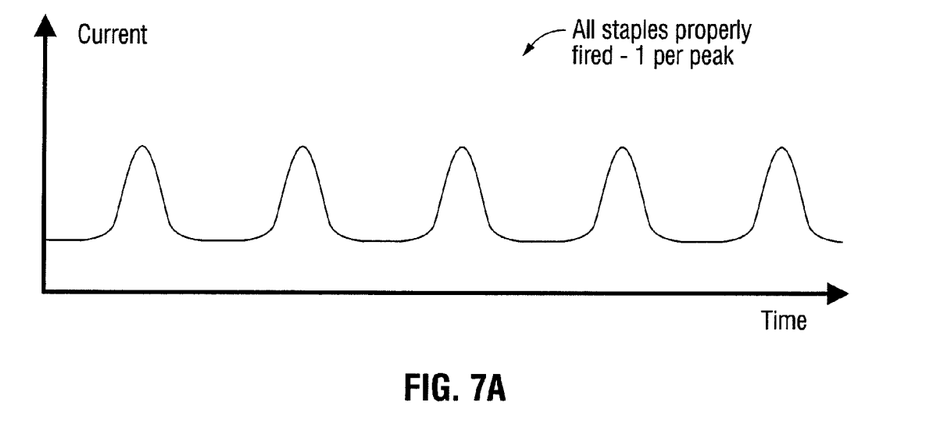
FIGS. 7a to 7d illustrate current profiles associated with different stapling events.

As indicated above, after the target position is reached at B, the motor may be controlled to maintain a force necessary to maintain the target position. The current driving the motor may be monitored at this stage for a variety of purposes. For example, where the device is, e.g., a surgical stapler, a profile of the measured current may be used to identify whether all of the staples of a staple cartridge have fired. FIG. 7a illustrates an expected current profile during a stapling procedure as a driver, e.g., a wedge, sequentially drives five staples. It should be understood that any number of staples may be provided and the firing of five staples is for illustration purposes. The peaks in the current measurement correspond to the increased force or power necessary to hold the tissue gap with the staple be forced between the clamping elements, e.g., the jaws of a linear stapler. If the firing is initiated and a current profile that closely resembles FIG. 7a results, it may be determined that all of the staples properly driven or fired.

Figure 7B:
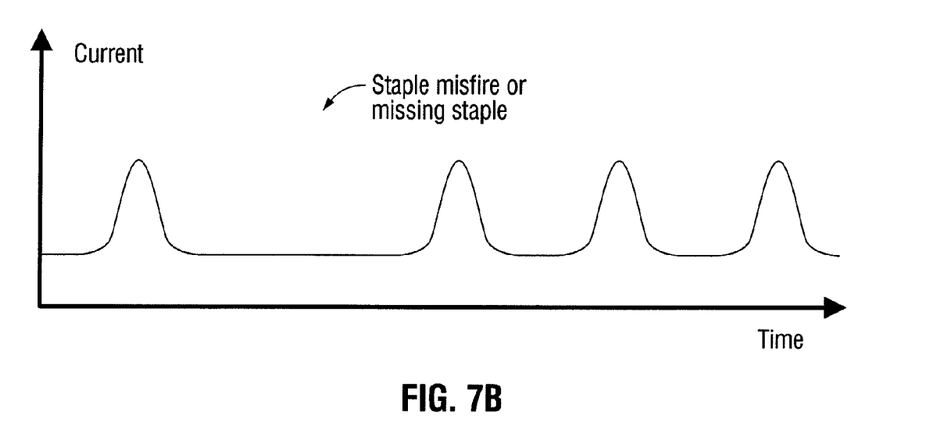

If the staple driving procedure is initiated and results in a current profile as illustrated in FIG. 7b, it may be determined from the lack of a peak that the second staple position was not properly driven or fired, e.g., due to a misfire or a missing staple from the staple cartridge. A misfire may similarly be shown, e.g., when a current peak is present, but substantially lower than expected.

Figure 7C:
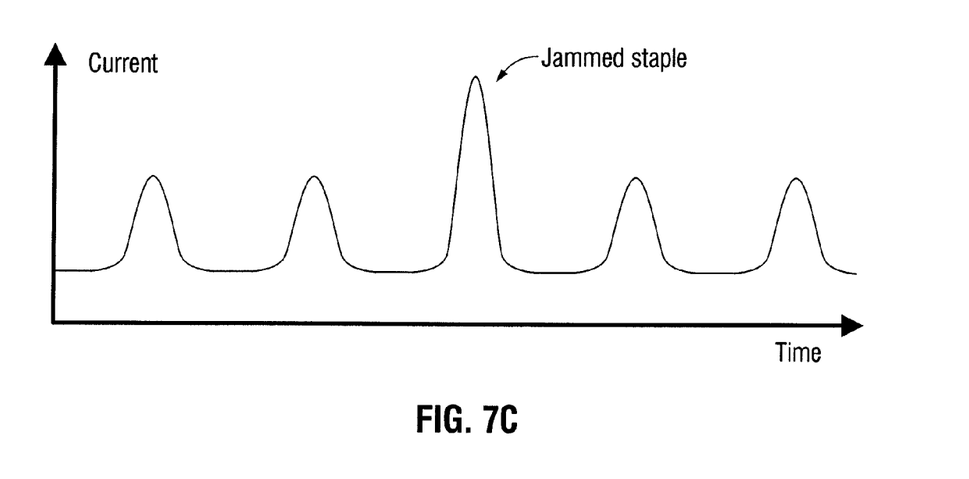

If the staple driving procedure is initiated and results in a current profile as illustrated in FIG. 7c, it may be determined that the staple in the third staple position jammed in some manner, resulting in the higher peak current measurement.

Figure 7D:
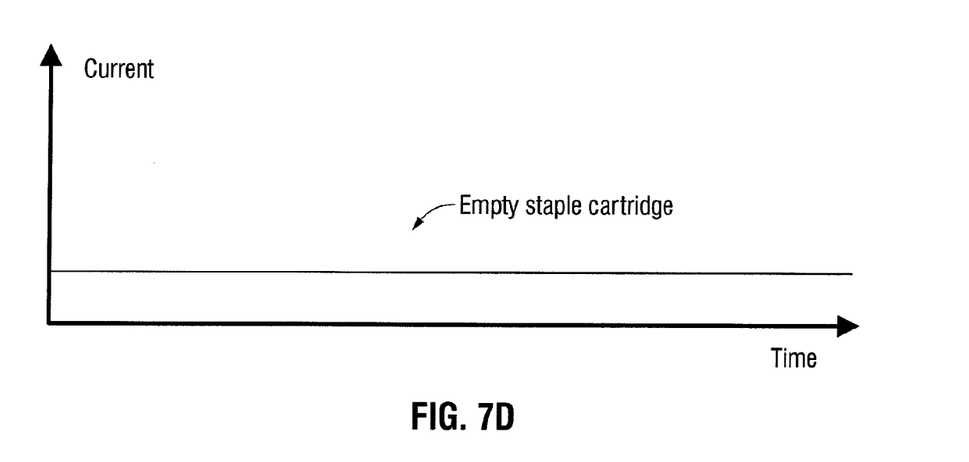

If the staple driving procedure is initiated and results in a current profile as illustrated in FIG. 7d, it may be determined that the staple cartridge is empty or that a staple cartridge is not present.

If any of these unexpected events occur, the control system may alert the user, e.g., by emitting an audible alarm and/or displaying an error message on a computer screen. The control system also may abort the staple firing, and or enter a different control algorithm.

Moreover, a profile of the current measurements may be used to monitor and track structural fatigue in at least one of the clamping members, e.g., by comparing to a normal current or motor signature. In this regard, a current profile may indicate, e.g., flexure due to plastic deformation resulting from fatigue failure. Further, the current profile may be used to track accumulated fatigue by determining the amount of force and the number of cycles exerted by a clamping member.

It should be appreciated that example methods according to the present invention may be implemented using any appropriate control system, e.g., a digital and/or analog control system, which may be integrated into the medical device or may be remotely located, whereby control and feedback signals are communicated via, e.g., a wireless or wired interface. The control system may have a display output, e.g., a monitor, and/or inputs to communicate with, e.g., a surgeon. The display output may display data relevant to the procedure including, e.g., the current closing rate, compressive force, and/or tissue gap. The control system may run predefined control programs or algorithms that may be pre-selected for the particular device. The control system may additionally or alternatively ask for inputs from the operator to define the parameters of the tissue compression control.

Further, the compressibility of the tissue may be determined by examining the current applied to the motor as compared with the closing rate. For example, if the measured current is very high when using a low closing rate, the tissue is less compressible than situations where the current is low for a higher closing rate.

While a tissue gap of 1 mm is mentioned above as an example of a desired tissue gap appropriate for tissue stapling, it should be appreciated that instead of an absolute distance measurement for the gap, alternative gap parameters may be provided. For example, one or more optical sensors may be provided to measure blood flow across one or more staple lines as a measure of desired tissue gap. Furthermore, oxygen saturation may be used in connection with the determination of the desired tissue gap. Moreover, the ratio of compressed to uncompressed tissue, e.g., based on the power applied to the tissue at the knee in the graphs of FIGS. 1 and 2, may form the basis of the desired tissue gap.

What is claimed is:

1. A method, comprising:
   clamping tissue between a first clamping member and a second clamping member by driving at least one of the clamping members with an electric motor toward a predetermined tissue gap between the clamping members;
   during the clamping, monitoring a parameter of the electric motor indicative of a clamping force exerted to the tissue by the clamping members; and
   during the clamping, controlling the electric motor, based on the monitored parameter, to limit the clamping force to a predetermined maximum limit.

2. The method of claim 1, wherein the predetermined maximum limit is selected based on predetermined properties of the tissue to be clamped.

3. The method of claim 2, wherein the predetermined maximum limit is selected to limit trauma to the clamped tissue to a predetermined acceptable level.

4. The method of claim 1, wherein the predetermined maximum limit is below a predetermined deflection limit of the at least one of the clamping members.

5. The method of claim 1, wherein the controlling includes adjusting a voltage applied to the electric motor.

6. The method of claim 1, wherein the controlling includes limiting the current driving the electric motor.

7. The method of claim 1, wherein the monitoring includes measuring a current driving the electric motor.

8. The method of claim 7, further comprising:
   prior to the clamping, measuring current due to frictional losses associated with moving the clamping members; and
   subtracting the frictional losses from the current measured during the clamping.

9. The method of claim 7, further comprising, prior to the clamping, measuring a current offset.

10. The method of claim 9, further comprising subtracting the current offset from the current measured during the clamping.

11. The method of claim 1, wherein the predetermined maximum limit is selected to prevent the force from reaching a yield force.

12. The method of claim 1, wherein the predetermined maximum limit is selected to prevent the clamping members from splaying.

13. The method of claim 1, further comprising using a profile of the monitored parameter to monitor and track structural fatigue in at least one of the clamping members.

14. The method of claim 13, wherein the profile is compared to a normal parameter signature.

15. The method of claim 1, wherein the surgical instrument is a surgical stapler and one of the clamping members is an anvil configured to form surgical staples.

16. The method of claim 15, further comprising using a profile of the monitored parameter to identify whether all of the staples of a staple cartridge have fired.

17. The method of claim 15, further comprising using a profile of the monitored parameter to identify at least one of staple misfires, an absence of staples in a staple cartridge, and staple jams.

18. The method of claim 1, wherein the controlling includes:
   determining a motor velocity;
   determining a motor position; and
   determining a net motor current attributable to the compression by subtracting out a current offset and current due to frictional losses.

19. The method of claim 18, wherein the controlling further comprises:
   determining a velocity drive based on the determined velocity;
   determining a position drive based on the determined position; and
   determining a current drive based on the determined net motor current.

20. The method of claim 19, wherein the controlling further comprises applying the smallest of the velocity drive, the position drive, and the current drive to the motor.

21. The method of claim 18, further comprising detecting the presence of an incompressible object based on the motor velocity.

22. The method of claim 1, wherein the controlling includes adjusting a driving speed of the motor to limit the clamping force to the predetermined maximum limit.

* * * * *